(12) United States Patent
Treacy

(10) Patent No.: US 9,098,604 B2
(45) Date of Patent: Aug. 4, 2015

(54) SYSTEM AND METHOD FOR MONITORING CLINICIAN RESPONSIVENESS TO ALARMS

(75) Inventor: Stephen Thomas Treacy, Menomonee Falls, WI (US)

(73) Assignee: General Electric Company, Schenectady, NY (US)

(*) Notice: Subject to any disclaimer, the term of this patent is extended or adjusted under 35 U.S.C. 154(b) by 502 days.

(21) Appl. No.: 13/334,211

(22) Filed: Dec. 22, 2011

(65) Prior Publication Data
US 2013/0162424 A1  Jun. 27, 2013

(51) Int. Cl.
G06Q 10/06 (2012.01)
G06F 19/00 (2011.01)
G06Q 10/10 (2012.01)
G08B 25/14 (2006.01)
G06Q 50/22 (2012.01)

(52) U.S. Cl.
CPC ........ G06F 19/327 (2013.01); G06Q 10/06393 (2013.01); G06Q 10/10 (2013.01); G06Q 10/0639 (2013.01); G06Q 10/06395 (2013.01); G06Q 10/06398 (2013.01); G06Q 10/063112 (2013.01); G06Q 50/22 (2013.01); G08B 25/14 (2013.01)

(58) Field of Classification Search
CPC ................... G06Q 10/0639; G06Q 10/06393; G06Q 10/06395; G06Q 10/06398; G06Q 10/063112; G06F 19/327; G08B 25/14
USPC ............ 340/502; 705/2, 7.38, 7.42, 345, 7.39
See application file for complete search history.

(56) References Cited

U.S. PATENT DOCUMENTS

| | | | |
|---|---|---|---|
| 6,585,645 B2 | 7/2003 | Hutchinson | |
| 7,920,061 B2 | 4/2011 | Klein et al. | |
| 7,967,749 B2 | 6/2011 | Hutchinson et al. | |
| 2001/0034631 A1* | 10/2001 | Kiselik | 705/8 |
| 2008/0010093 A1* | 1/2008 | LaPlante et al. | 705/3 |
| 2008/0015900 A1 | 1/2008 | Denholm | |
| 2009/0054736 A1 | 2/2009 | Rantala et al. | |
| 2009/0256709 A1 | 10/2009 | Davis | |
| 2009/0275807 A1 | 11/2009 | Sitzman et al. | |
| 2010/0259395 A1 | 10/2010 | Nuthi | |
| 2011/0169644 A1* | 7/2011 | Muhsin et al. | 340/573.1 |
| 2011/0291838 A1 | 12/2011 | Rantala | |

OTHER PUBLICATIONS

Search Report and Written Opinion from GB Patent Application No. 1222234.5 dated May 29, 2013.

* cited by examiner

*Primary Examiner* — Ariel Balaoing
*Assistant Examiner* — Benyam Haile
(74) *Attorney, Agent, or Firm* — Andrus Intellectual Property Law, LLP

(57) ABSTRACT

A method of monitoring clinician responsiveness to alarms generated by patient monitors. The method includes the steps of: receiving an alarm event from a patient monitor at a central monitor, determining an alarm initiation time for the alarm events, receiving at the central monitor an acknowledgement of the alarm event by a clinician, calculating an event response time as the time between the alarm initiation time and the acknowledgement of the alarm event by the clinician, determining a total number of alarm events, determining event response times for each of the total number of alarm events, and computing a responsiveness score based on the event response time for each of the total number of alarm events.

16 Claims, 3 Drawing Sheets

SYSTEM AND METHOD FOR MONITORING CLINICIAN RESPONSIVENESS TO ALARMS

BACKGROUND

Patient monitoring devices, such as devices monitoring a patient's vital signs, are designed to identify physiological problems experienced by patients and to alert clinicians to those problems. Typically, clinicians are alerted to such problems via the generation of alarms, such as auditory or visual alarms, or alerts sent directly to pagers or personal digital assistants (PDAs) carried by clinicians. Alarms may also be generated by patient monitors when problems occur with the monitor itself, such as a low battery, disconnection of patient monitoring lead, etc.

Hazards may arise when alarms go unrecognized or are not acted upon for a period of time. Clinicians responsible for monitoring patient alarms may receive frequent visual and audio alarm notifications for those alarms. Such repetitive exposure to alarm notifications can cause a clinician to become de-sensitized to the alarms, which affects the timeliness of his or her responses. Additionally, clinicians may begin to ignore alarms as a result of the frequent occurrence of false alarm events, which may cause the clinician to believe the alarms are unimportant and do not need a response.

Alternatively, a clinician may desire to attend to all alarm events, but may be unable to respond to alarm events in a timely manner because the clinician's work flow is too heavy. Several alarms may occur at once, and/or a hospital floor may be understaffed, which may create a scenario in which it is impossible for a clinician to respond to all alarm events in a timely manner.

Unheeded alarms negatively affect patient care, and can lead to undesired outcomes for patients. An alarm event may indicate a deterioration of a patient's physiological condition, which often requires immediate attention. Alternatively, technical alarms may occur that indicate the inability of a patient monitor to accurately monitor a patient's condition.

Thus, methods and systems are needed for monitoring and measuring clinicians' responses to alarms.

SUMMARY

The present disclosure stems from the inventor's research and development of methods and systems for monitoring and analyzing clinicians' responsiveness to alarm events. The present inventor has recognized that prior art monitoring systems do not provide a way for hospitals or medical facilities to monitor how and when clinicians are responding to alarms generated by patient monitors. The present inventor further recognized that methods and systems are needed for determining when and to what extent clinicians are experiencing alarm fatigue, and for analyzing trends in clinician responsiveness to alarms. The inventor also recognized that such systems and methods would allow hospitals and medical facilities to maintain a high level of medical care by establishing a system which encourages clinicians to respond to alarm events in a timely manner and allows monitoring of such responses. Further, such a system allows a facility to optimize its workflow and identify and alleviate problems which may arise involving alarm fatigue.

One embodiment relates to a method of monitoring clinician responsiveness to alarms generated by patient monitors comprising the following steps: receiving an alarm event from a patient monitor at a central monitor, determining an alarm initiation time for the alarm event, receiving at the central monitor an acknowledgement of the alarm event by a clinician, calculating an event response time as the time between the alarm initiation time and the acknowledgement of the alarm event by the clinician, determining a total number of alarm events, determining event response times for each of the total number of alarm events, and computing a responsiveness score based on the event response time for each of the total number of alarm events. The method of claim 1 may further include the step of determining an allowable response period for the alarm event received at the central monitor, and computing the responsiveness score based further on a comparison between the event response time and the allowable response period. Various rules are entered into the system to determine when alerts are generated to administrators based on either one or a series of responsiveness scores for the clinician. If the responsiveness score or scores indicate that one or more clinicians are not being sufficiently responsive to alarms, alerts may be generated to notify an administrator of the insufficient responsiveness. Additionally, reports may be generated to summarize responsiveness scores and/or indicate trends in responsiveness scores.

Another embodiment relates to a method of monitoring clinician responsiveness to alarms including the following steps: receiving at a central monitor a notification of an alarm event from a patient monitor wherein the notification includes an alarm initiation time and an alarm type, determining an allowable response period for the alarm event based on the alarm type, receiving at the central monitor an acknowledgement of the alarm event by a clinician, calculating an event response time as the time between the alarm initiation time and the acknowledgement of the alarm event, and computing a responsiveness score based on the event response time and the allowable response period. The method may further include the step of determining a total number of alarm events, and the responsiveness score may be further based on the total number of alarm events. For example, the responsiveness score may be equal to a percentage of the total alarm events wherein the response time is less than the allowable response period.

Yet another embodiment relates to a system for monitoring clinician responsiveness to alarms. The system comprises a patient monitor, a central monitor, and a control unit. The patient monitor is configured to receive physiological patient data, detect the occurrence of an alarm condition, and transmit notification of that alarm condition. The central monitor is configured to receive the notification of the alarm condition from the patient monitor, and to also receive an acknowledgement of the alarm condition by a clinician. The control unit is configured to receive the notification of the alarm condition and the acknowledgement of the alarm condition from the central monitor, calculate an event response time as the time it took the clinician to acknowledge the alarm condition, determine a total number of alarm events, compute a responsiveness score based on the event response time for each of the total number of alarm events, and store the responsiveness score on a computer readable memory device.

Other principles, features and advantages of the invention will become apparent to those skilled in the art upon review of the following drawings, the detailed description, and the appended claims.

BRIEF DESCRIPTION OF THE DRAWINGS

The drawings illustrate the best mode presently contemplated of carrying out the disclosure. In the drawings.

DETAILED DESCRIPTION OF THE DRAWINGS

In the present description, certain terms have been used for brevity, clarity and understanding. No unnecessary limitations are to be implied therefrom beyond the requirement of the prior art because such terms are used for descriptive purposes only and are intended to be broadly construed. The different systems and methods described herein may be used alone or in combination with other systems and methods. Various equivalents, alternatives, and modifications are possible within the scope of the appended claims. Each limitation in the appended claims is intended to evoke interpretation under 35 USC §112, sixth paragraph, only if the terms "means for" or "step for" are explicitly recited in the respective limitation.

Figure 1:
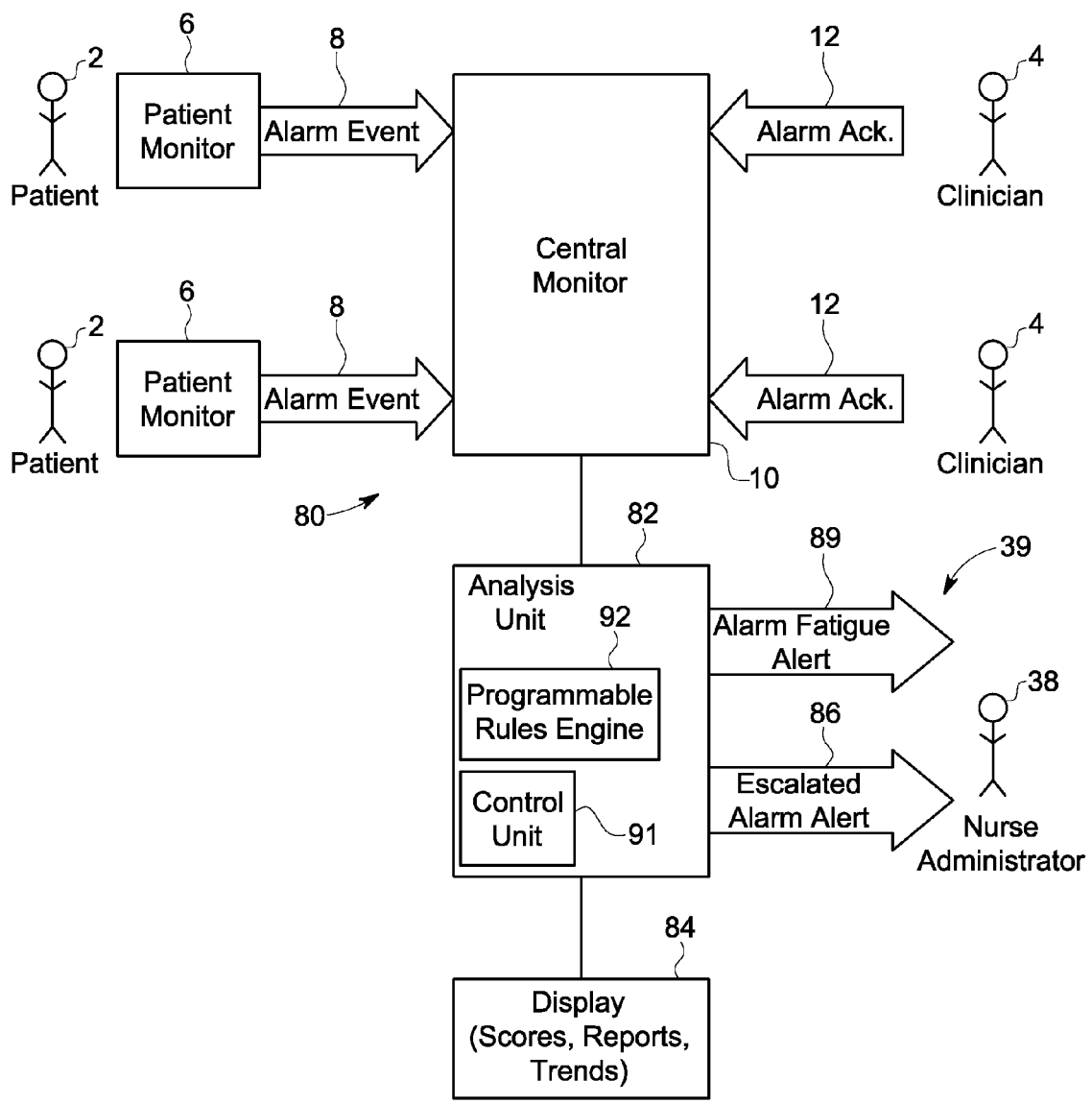
FIG. 1 is a schematic of an embodiment of a system and method for monitoring clinician responsiveness to alarms.

Referring to FIG. 1, a monitoring system 80 may include a central monitor 10 configured to receive alarm events 8 generated by one or more patient monitors 6 connected to one or more patients 2. The central monitor 10 may also be configured to receive alarm acknowledgements 12 by clinicians 4. The monitoring system 80 may have an analysis unit 82 which processes alarm event data and alarm acknowledgement data acquired by the central monitor and produces an output. The output from the analysis unit 82 may be in form of scores, reports, trends, or any other format known in the art as appropriate for conveying such statistical or qualitative information.

Figure 2:
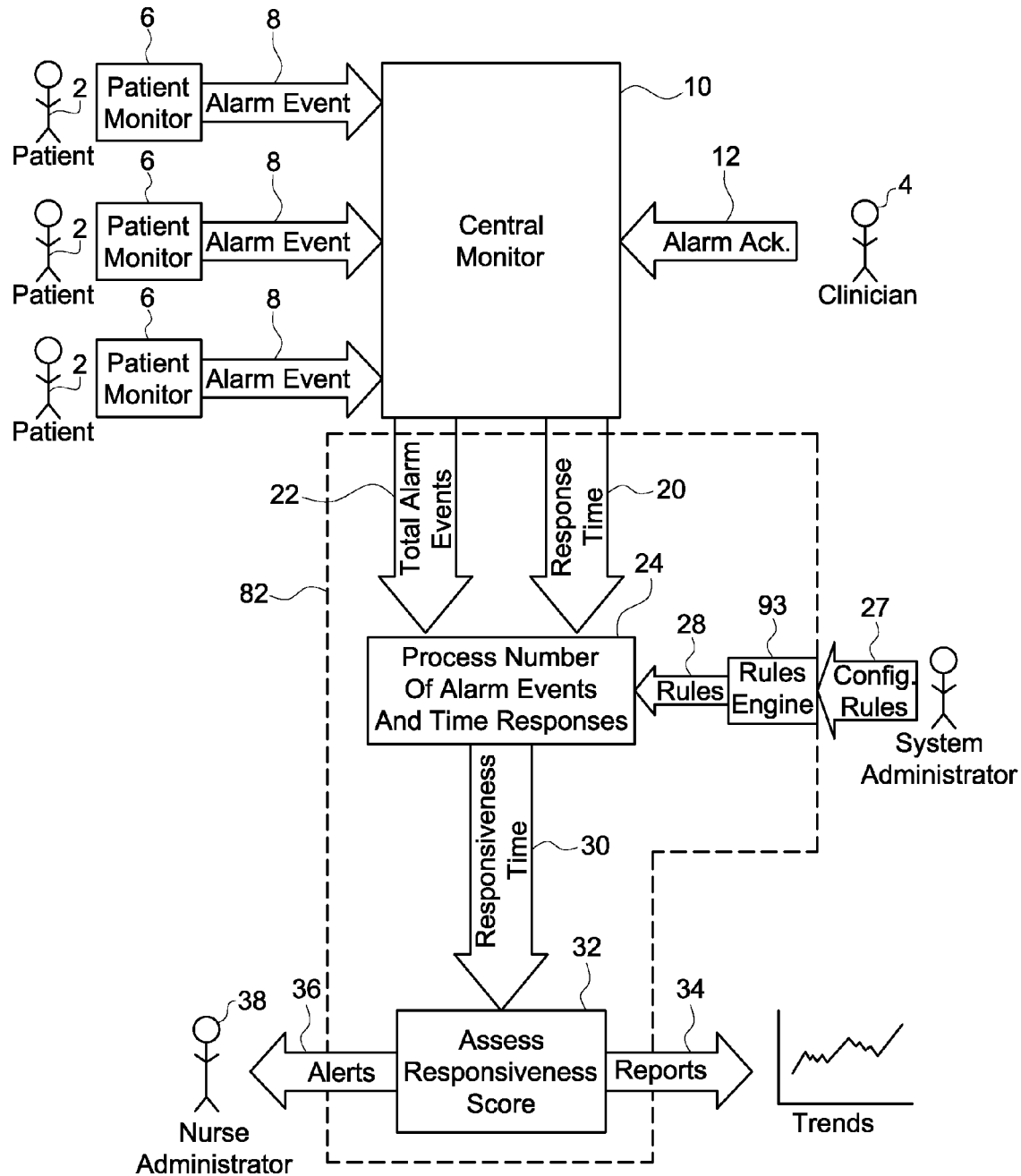
FIG. 2 is a schematic of another embodiment of a system and method for monitoring clinician responsiveness to alarms.

The analysis unit 82 has a control unit 91 that orchestrates the alarm analysis process. The analysis unit 82 receives data input from the central monitor 10, including information regarding alarm events 8 and/or alarm acknowledgements 12. The analysis unit 82 processes data received from the central monitor 10 according to rules established by the programmable rules engine 92. As depicted in FIG. 2 and explained further below, the programmable rules engine 93 may contain a set of rules 28 for processing 24 alarm events 8 and response times 20.

Referring to both FIGS. 1 and 2, the analysis unit 82 may detect the presence of hazardous situations, such as a clinician 4 experiencing alarm fatigue or an alarm event that has not been acknowledged after a long period of time, In response to the detection of such a hazard, the analysis unit 82 may generate an alert 36 to inform the appropriate party of the hazard. For example in FIG. 1, upon detection of an alarm event that has not been acknowledged, the analysis unit 82 may generate an escalated alarm alert 86 to alert a nurse administrator 38 to the missed alarm. As another example, the analysis unit 82 may generate an alarm fatigue alert 89 to the administrator 38 if it detects the possibility of a clinician 4 who may be experiencing alarm fatigue. The purpose of the alarm fatigue alert is to alert an administrator 38 when a clinician has become de-sensitized to alarms due to suffering frequent alarm notifications for a period of time such that the clinicians' responsiveness to alarms is lagging. The alarm fatigue alert may be generated to alert a nurse administrator 38 if a responsiveness score 30 falls below a threshold level. Alternatively, an alarm fatigue alert may be generated if the responsiveness score 30 trends downward at a specified rate.

The output produced by the analysis unit may be received by a display 84. The display 84 may be configured to display any information transmitted by the analysis unit 82, including responsiveness scores 30, alerts 36, or reports 34. The display 84 may be a central display screen, for example at a nurses' station. Alternatively, the display 84 could be any number of personal displays, including personal computer displays, hand held displays, pagers, or the like. The purpose of the display 84 is to transmit information from the analysis unit 82 to an appropriate nurse administrator or clinician. The central monitor 10 and the analysis unit 82 may be integrated into one device that is controlled by a single control unit, or they may be two separate devices with two separate control units. Likewise, the display unit may be integrated with either the central monitor 10 and/or the analysis unit 82.

FIG. 2 depicts another embodiment of a system and method for monitoring clinician responsiveness to alarms. The patient monitor 6 collects physiological data from a patient 2 and generates an alarm event 8 upon detection of an alarm condition. The patient monitor 6 may also generate an alarm event 8 if it encounters a technical problem that needs to be remedied by a clinician or other staff member. The alarm events 8 are detected by a central monitor 10. The central monitor 10 may also detect specifics regarding the alarm event, such as the type of alarm generated, the reason for the alarm generation, the time that the alarm was initiated, the severity of the alarm, etc.

The central monitor 10 may also detect when an alarm is acknowledged by a clinician 4. Alarm acknowledgements 12 may be made by a clinician 4 in any way known in the art. For example, clinicians 4 may acknowledge alarms at the patient monitor 6 where the alarm occurred. The alarm acknowledgement 12 may include remedying the condition which generated the alarm event 8. The patient monitor 6 could then detect that the alarm condition has been remedied and could terminate the alarm event 8. For example, in the instance of a technical alarm, such as a low battery in a patient monitor 6, the clinician 4 may remedy the technical alarm by replacing the battery in the patient monitor 6. The patient monitor 6 would then terminate the alarm event 8 generated in response to the low battery alarm. The central monitor 10 may recognize the termination of the alarm event as an alarm acknowledgement 12 by the clinician 4. Alternatively, a clinician 4 may acknowledge 12 an alarm event 8 by clicking on an acknowledgement button on a display screen of the patient monitor 6, or on a display screen at a central monitoring station.

The central monitor 10 relays the alarm event information and/or the alarm acknowledgement information to the analysis unit 82. The analysis unit 82 analyzes the alarm event information and alarm acknowledgement information and produces information summaries and reports regarding clinician responsiveness to alarm events. The analysis unit 82 may calculate a response time 20 for a particular alarm event 8, such as by calculating the time between the initiation of the alarm event 8 and the alarm acknowledgement 12 by the clinician 4.

The analysis unit 82 may also calculate an alarm event total 22. The total alarm events 22 may represent a summation of all the alarm events occurring in a particular area of the medical facility in a particular period of time. Alternatively, the total alarm events may represent the total number of a certain type of alarm event, such as a critical alarm event. In still other embodiments, the total alarm events 22 may represent a summation of the alarm events generated by a particular patient monitor 6 within a certain period of time. In still other embodiments, the total alarm events 22 may represent a summation of the alarms acknowledged by a particular clinician 4 or a group of clinicians over a specified period of time.

The analysis unit 82 may process 24 the total number of alarm events 22 and the response time 20 for each of the events therein. The analysis unit 82 may process the data according to rules 28 generated by the programmable rules engine 93. The programmable rules engine 93 can be configured as shown by arrow 27, such as by a system administrator 26. The programmable rules engine 93 may contain a set of rules for processing 24 alarm events and response times. For example, the rules 28 of the programmable rules engine 93 may dictate how alarm events are to be processed or weighted based on the type of alarm which initiated the alarm event 8—e.g., responsiveness data regarding critical alarms is weighted more heavily than that regarding non-critical alarms. Other rules 28 may dictate the determination of an allowable response period for each alarm event. The allowable response period set by a rule 28 may be a maximum amount of time in which a clinician should acknowledge or respond to an alarm event. The rule 28 may dictate the calculation of the allowable response period based on information about the alarm event gathered by the central monitor, such as the type of alarm or the severity of the alarm. Other rules 28 set out in the programmable rules engine 93 regard the processing of alarm information based on the number of pending, unacknowledged alarm events, the number of alarm events occurring simultaneously or at overlapping times, the number of clinicians available to attend to alarms, and/or the alarm acknowledgement history of the attending clinicians.

The analysis unit 82 processes 24 the total alarm events 22, the response time 20, and other alarm-related information to produce a responsiveness score 30. The responsiveness score 30 may represent the responsiveness of a clinician 4 to the total number of alarm events 22. Alternatively, the responsiveness score 30 may represent the responsiveness of a group of clinicians, or the responsiveness of all clinicians in a medical facility, or a portion thereof. In still other embodiments, the responsiveness score 30 may be based on responses to a representative set of alarm events, or to the alarm events occurring over a particular period of time, or a particular portion of clinicians' shifts. In still other embodiments, the responsiveness score 30 may represent the responsiveness of one or more clinicians to a particular type of alarm event 8, such as a critical alarm, a cardiac alarm, a blood pressure alarm, a respiratory alarm, a technical alarm, etc.

The responsiveness score 30 may be calculated according to various different scoring systems depending upon user requirements. For example, the responsiveness score could be calculated based upon the total alarm events 22 and their response times 20—e.g., based on a simple average of the alarm response times. Alternatively, the score could reflect rated analysis dictated by the programmable rules engine 93, such as rules weighting the severity of each alarm, the demand placed on the clinician during the response period due to the occurrence of simultaneous or overlapping alarm events, a clinicians' response history, etc. Additionally, the responsiveness score may account for the comparison of the response times to the allowable response period. For example, the response score may be a percentage of the total alarm events 22 in which the response times 20 were less than or equal to the allowable response period.

The responsiveness score 30 could be expressed according to any scale or system. For example, the responsiveness score 30 could be expressed on a 1 to 10 scale, or on a traditional A to F grading scale. In other embodiments, the responsiveness score 30 could be more nuanced and convey more detailed information. For example, the score could have multiple parts or sections, each conveying information about quality and/or quality of a clinician's responsiveness to different types of alarm events or alarm events occurring at different times during a shift. In still other embodiments, the responsiveness score could be a sliding scale with one end representing perfect responsiveness wherein a clinician responded to all alarms in a minimum amount of time and the other end representing poor responsiveness wherein a clinician fails to acknowledge any alarm events within the allowable response period. Such a sliding scale could account for any number of rules 28, and thus could represent a varying level of complexity based on the configuration of the programmable rules engine 93.

Upon calculating a responsiveness score 30, the analysis unit 82 may communicate the responsiveness score to a nurse administrator 38 or other administrator through a display or some other communication device. Alternatively or additionally, the analysis unit 82 may produce alerts 36 or reports 34.

Alerts 36 may be generated by the analysis unit 82 if the responsiveness score reflects poor responsiveness to alarm events 8. Such alerts 36 may include escalated alarm alerts, alarm fatigue alerts, or alerts as to trends in responsiveness score, such as trends representing a decrease in clinician responsiveness. Such alerts may be transmitted to a nurse administrator 38, or another appropriate individual, via any means known in the art for transmitting an alarm notice. For example, the alert may be transmitted through an auditory alarm, a visual alarm, a notification on a display, or through a personal device, such as a pager or a PDA.

Other alerts 36 may also be generated by the analysis unit 82. For example, an alert 36 may be generated to alert an administrator if a large number of alarm events 8 are pending simultaneously. Such an alert would help the administrator allocate staffing and other resources appropriately so that all alarm events could be attended to in a timely manner. Conversely, the analysis unit 82 could generate an alert 36 upon detecting an abundance of clinicians in an area where no alarm events are occurring. Again, that alert could allow an administrator to optimize staffing and resources.

The analysis unit 82 may also assess 32 the responsiveness score 30 to generate reports 34. The reports 34 could convey any information about alarm events or clinician responses thereto. For example, the reports 34 could convey trends in clinician responsiveness to alarms according to time of day, shift duration, staffing members, alarm type, frequency of alarms, etc. The reports 34 may identify periods where clinician responsiveness to alarms was relatively poor and may identify reasons for such poor responsiveness. For example, the reports 34 may identify periods of time where the number of alarm events was relatively high and/or the number of available clinicians was relatively low. Additionally, the reports 34 may identify periods where clinicians experience alarm fatigue.

Figure 3:
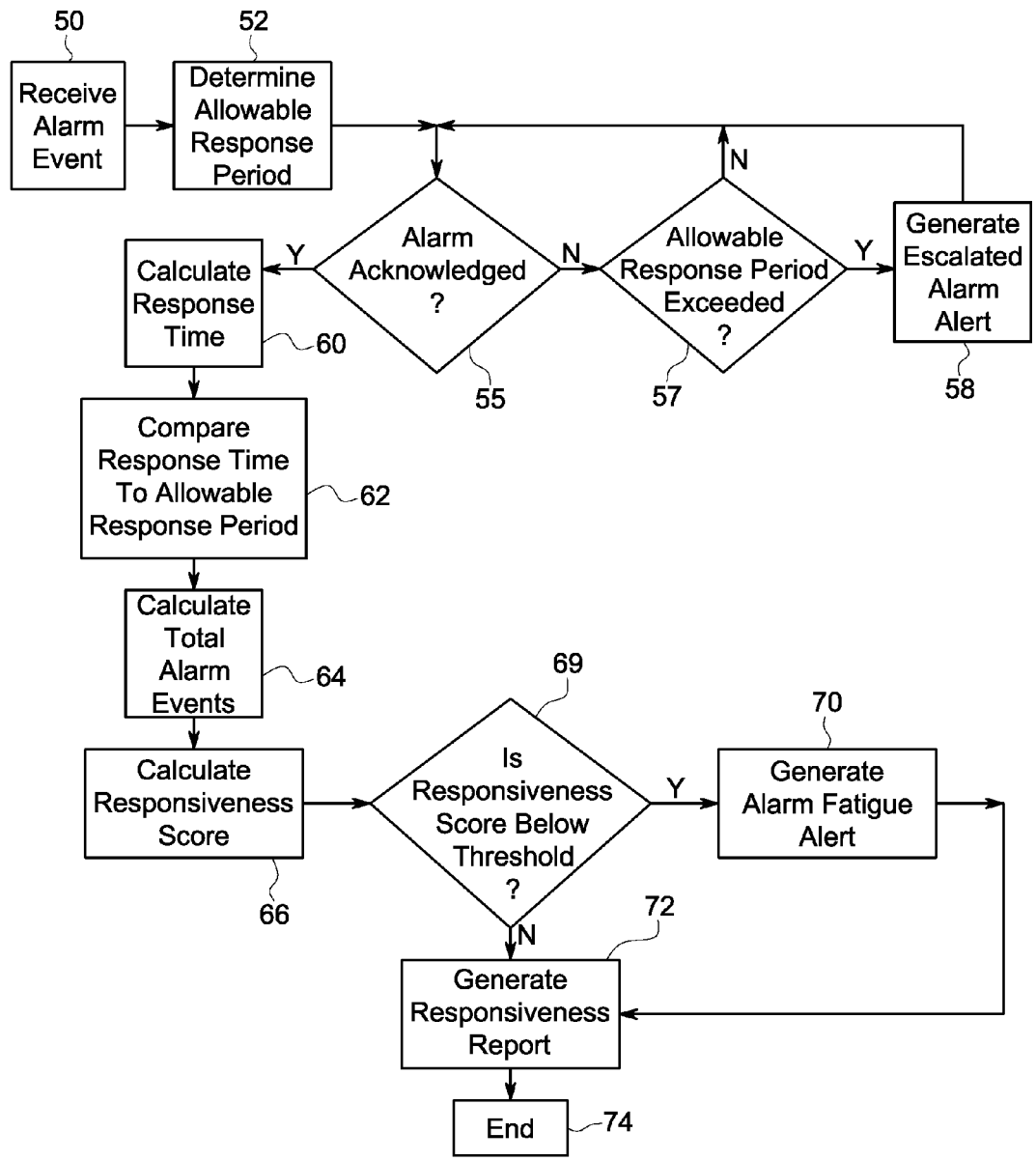
FIG. 3 is a flowchart of the steps performed in an exemplary method of monitoring clinician responsiveness to alarms.

Referring to FIG. 3, the flowchart depicts one embodiment of a method of monitoring clinician responsiveness to alarms. Initially, an alarm event is received 50, for example at a central monitor. The alarm event data received may include details regarding the alarm event, including the type of alarm that generated the event, the criticality or severity of the condition that generated the alarm, and/or the initiation time of the alarm. Upon receiving the alarm event at block 50, the control unit may determine the allowable response period, block 52, for the particular alarm event. The determination of the allowable response period may be based on the type or severity of the alarm event received at block 50.

Following its determination of the allowable response period 52, the control unit transitions to block 55 wherein it determines whether the alarm condition has been acknowledged by a clinician. If the alarm condition has not been acknowledged, the control unit determines whether or not the allowable response period has been exceeded, block 57. If the allowable response period has not been exceeded, the control unit cycles back to block 55, where it checks again to see if the alarm event has been acknowledged by a clinician. At block 57, if the allowable response period has been exceeded, the control unit may generate an escalated alarm alert, block 58, to alert an administrator to the fact that the alarm event has not been acknowledged within the allowable response period. The control unit then cycles back to block 55 where it checks again to see if the alarm event has been acknowledged.

Once the alarm event is acknowledged by a clinician at block 55, the control unit calculates the response time at block 60. The response time may be calculated as the period between the alarm initiation time and the time that the alarm is acknowledged. Alternatively, the response time may be calculated as the period between the time that the alarm event was received at block 50 and the time that the alarm was acknowledged at block 55. Next, at block 62, the control unit compares the response time calculated at block 60 to the allowable response period calculated at block 52. The control unit then calculates the total alarm events at block 64 and transitions to block 66, where it calculates a responsiveness score based on the determinations made at blocks 62 and 64.

At block 69, if the responsiveness score is below a threshold, the control unit may generate an alert, block 70, such as an alarm fatigue alert. The threshold for judging the responsiveness score may be a particular score below which a responsiveness score may be determined to be unacceptable. Alternatively, the threshold may be a trend in a series of responsiveness scores, which has been determined to be the cutoff between an acceptable responsiveness trend and an unacceptable responsiveness trend.

If the responsiveness score is above the threshold, as determined by the control unit at block 69, the control unit may proceed to generate a responsiveness report at block 72. Either way, whether or not the responsiveness score is above or below the threshold, the control unit will eventually proceed to block 72 where it generates one or more responsiveness reports, block 72, before terminating its process at block 74.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements and/or method steps that do not differ from the literal language of the claims, or if they include equivalent structural elements and/or method steps with insubstantial differences from the literal languages of the claims.

I claim:

1. A method of monitoring clinician desensitization to alarms generated by patient monitors, the method comprising:
   receiving a plurality of alarm events from one or more patient monitors at a central monitor;
   determining an alarm initiation time for each of the alarm events;
   receiving at the central monitor an acknowledgement from the clinician of each of the alarm events;
   calculating an event response time for each of the plurality of alarm events as the time between the alarm initiation time and the acknowledgement of the alarm event by the clinician;
   computing a responsiveness score based on the plurality of event response times for the plurality of alarm events, wherein the responsiveness score is indicative of a level of alarm fatigue experienced by the clinician over the plurality of alarm events; and
   generating an alarm fatigue alert when the responsiveness score trends downward at a rate greater than a threshold rate.

2. The method of claim 1, further including the step of determining an allowable response period for each of the alarm events received at the central monitor.

3. The method of claim 2, wherein the allowable response period is determined based on the type of alarm event received for the patient monitor, wherein the allowable response period is shorter for more critical types of alarm events.

4. The method of claim 2, wherein the allowable response period is determined based on severity of the alarm event, wherein the allowable response period is shorter for more severe alarms.

5. The method of claim 2, further including the step of transmitting an escalated alarm alert if the alarm event has not been acknowledged within the allowable response period.

6. The method of claim 2, wherein the responsiveness score is further computed based on a comparison between the event response time and the allowable response period.

7. The method of claim 6, wherein the responsiveness score is equal to a percentage of the total alarm events wherein the response time is less than the allowable response period.

8. The method of claim 1, further including the step of generating an alarm responsiveness report.

9. The method of claim 8, wherein the responsiveness report includes a trend analysis conveying changes in response score with respect to the clinician's shift duration.

10. The method of claim 8, wherein the responsiveness report includes a trend analysis conveying changes in response score with respect to a number of alarm events pending simultaneously.

11. The method of claim 1, wherein the alarm initiation time is the time that the alarm event was initiated at the patient monitor.

12. The method of claim 1, wherein the alarm initiation time is the time that the alarm event was received at the central monitor.

13. A method of monitoring clinician desensitization to alarms generated by patient monitors, the method comprising:
   receiving at a central monitor a notification of an alarm event from a patient monitor, wherein the notification includes an alarm initiation time and an alarm type;
   determining an allowable response period for the alarm event based on the alarm type;
   receiving at the central monitor an acknowledgement of the alarm event by a clinician;
   calculating an event response time for each alarm event as the time between the alarm initiation time and the acknowledgement of the alarm event;
   computing a responsiveness score for the clinician over a plurality of alarm events based on the event response time and the allowable response period for each of the plurality of alarm events, wherein the responsiveness score is indicative of a level of alarm fatigue experienced by the clinician over the plurality of alarm events; and
   generating an alarm fatigue alert when the responsiveness score trends downward at a rate greater than a threshold rate.

14. The method of claim 13, Wherein the responsiveness score is equal to a percentage of the total alarm events wherein the response time is less than the allowable response period.

15. The method of claim 13, further including the step of generating a responsiveness report, wherein the responsiveness report conveys trends in the response times to the alarm events.

16. A system for monitoring clinician desensitization to alarms, comprising:
- a patient monitor configured to receive physiological patient data, to detect an occurrence of an alarm condition, and to transmit notification of the alarm condition;
- a central monitor configured to receive the notification of the alarm condition from the patient monitor and to receive an acknowledgement of the alarm condition by a clinician; and
- a control unit configured to
  - receive the notification of the alarm condition and the acknowledgment of the alarm condition from the central monitor,
  - calculate an event response time as the time it took the clinician to acknowledge the alarm condition,
  - determine a total number of alarm events,
- compute a responsiveness score based on the event response time for each of the total number of alarm events: wherein the responsiveness score is indicative of a level of alarm fatigue experienced by the clinician, over the plurality of alarm events;
- generate an alarm fatigue alert when the responsiveness score trends downward at a rate greater than a threshold rate; and
- store the responsiveness score on a computer-readable memory device.

\* \* \* \* \*